(12) United States Patent
Yanof et al.

(10) Patent No.: US 6,505,065 B1
(45) Date of Patent: Jan. 7, 2003

(54) METHODS AND APPARATUS FOR PLANNING AND EXECUTING MINIMALLY INVASIVE PROCEDURES FOR IN-VIVO PLACEMENT OF OBJECTS

(75) Inventors: Jeffrey H. Yanof, Solon, OH (US); Paul Klahr, Beachwood, OH (US); Andy Ivan, Aurora, OH (US); Dave Hoffmeyer, Concord, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 257 days.

(21) Appl. No.: 09/697,805

(22) Filed: Oct. 27, 2000

Related U.S. Application Data
(60) Provisional application No. 60/162,407, filed on Oct. 29, 1999.

(51) Int. Cl.[7] .......................... A61B 5/055; G02B 23/26; A61N 5/10
(52) U.S. Cl. ...................... 600/427; 600/424; 600/103; 600/117
(58) Field of Search .................................. 600/427, 440, 600/443, 439, 444, 449, 424, 103, 117

(56) References Cited

U.S. PATENT DOCUMENTS

| | | | | |
|---|---|---|---|---|
| 4,930,525 A | * | 6/1990 | Palestrant | 128/898 |
| 5,155,435 A | | 10/1992 | Kaufman et al. | 324/309 |
| 5,638,819 A | | 6/1997 | Manwaring et al. | 600/424 |
| 2001/0040991 A1 | * | 11/2001 | Asano et al. | 382/128 |

FOREIGN PATENT DOCUMENTS

| | | | | |
|---|---|---|---|---|
| EP | 0 922 438 A1 | | 6/1999 | |
| EP | 0 995 406 A1 | | 4/2000 | |
| EP | 1 088 517 A1 | * | 4/2001 | A61B/6/00 |
| JP | 8-299363 A | * | 11/1996 | A61B/19/00 |
| JP | 2002-58751 | * | 2/2002 | A61N/5/10 |

OTHER PUBLICATIONS

Beyond Medicine—I.E.E.E. Engineering in Medicine & Biology; Mar./Apr., 1996.
3–D Imaging and Stereotactic Radiosurgery—I.E.E.E. Engineering in Medicine & Biology; Jul./Aug., 1997.
European Search Report dated Feb. 04, 2001.

* cited by examiner

*Primary Examiner*—Hieu T. Vo
(74) *Attorney, Agent, or Firm*—Fay, Sharpe, Fagan, Minnich & McKee, LLP

(57) ABSTRACT

A method (310) and apparatus (1) are provided for planning an executing minimally invasive procedures for in-vivo placement of objects within the body of a patient. The method and apparatus enable non-invasive pre-operation virtual seed placement and dose distribution planning using visualization information showing a patient's anatomy together with a set of single point targets (182) within the patient's body and a corresponding set of trajectories (184) through the skin and body of the patient leading to the selected target points. For enhanced visualization, multiplanar reformatted images (166, 168) are derived from CT image data sets and are angled to always contain the plane of the virtual needle (300) in the pseudo-axial image and its 90 degree slice counterpart. In an implementation stage, a stereotactic arm (40) spatially referenced to the patient's data set acts a needle guide (52) and is used to locate preplanned image planes containing virtual seed deposition points. A physical needle (50) is aligned with preplanned virtual needle trajectories (282, 284, 286) so that one or more seeds or other objects can be precisely placed within the patient's body.

19 Claims, 8 Drawing Sheets

METHODS AND APPARATUS FOR PLANNING AND EXECUTING MINIMALLY INVASIVE PROCEDURES FOR IN-VIVO PLACEMENT OF OBJECTS

CROSS-REFERENCE TO RELATED APPLICATIONS

This application claims the benefit of U.S. Provisional Application Serial No. 60/162,407 filed Oct. 29, 1999.

BACKGROUND OF THE INVENTION

The present invention relates to the art of interactive image-guided surgery and interactive surgical planning. It finds particular application in conjunction with the planning and implementation stages of minimally invasive stereotactic surgical procedures performed in CT imaging systems using a localization device to orient a surgical tool such as a brachytherapy needle or the like for planning and placement of objects within the body of a patient, and will be described with particular reference thereto. It is to be appreciated, however, that the invention is also applicable to a wide range of imaging equipment and techniques, for example ultrasonic and magnetic resonance imaging devices, and to a broad range of minimally invasive surgical procedures including many forms of surgery for placing objects at precise points within a patient such as interventional radiology procedures and others.

In certain surgical procedures, there is a need to place one or more objects at precise locations within the body of a patient. Examples of these procedures include techniques for placement of dental implants or other orthopedic supports or structures within a patient. One broad class of procedures that requires placement of objects within a patient are found in the interventional radiological arts. One such form of radiation therapy is brachytherapy in which radioactive seeds are inserted into cancerous tissue, thereby attacking cancer cells. In brachytherapy, as with other forms of radiation therapy, it is desirable that the seeds be distributed within the malignant tissue in a particular pattern according to a selected dose distribution plan. It is generally desirable that the seeds be distributed evenly so as to avoid hot (e.g., over-radiated), and cold (e.g., under-radiated) spots. Additionally, the seeds should not be placed outside of the target region. One method for inserting the seeds in the case of prostate brachytherapy involves trans-rectal ultrasound image guidance. One disadvantage of such a procedure, however, is that preoperative planning and visualization information is limited. Also, the procedure is uncomfortable for the patient.

Certain dose planning, preoperative planning, and post operative verification techniques have been proposed in radiation therapy to overcome the above disadvantages, particularly the lack of visualization information. In one example, the patient is first scanned to generate a volumetric image data set. Thereafter, the collected patient image data set is forwarded to an off-line dose planning system. On a remote computer, virtual "seeds" are placed on axial viewgraphs of the patient derived from the patient image data set to provide a virtual prescribed cumulative seed distribution. The location of the virtual seeds in x, y, z coordinates in the patient's image data set are stored so that when the patient is repositioned on the scanning apparatus, sometimes days later, the physical radioactive seeds can be introduced into the body of the patient at the physical x, y, z coordinates corresponding to the x, y, z coordinates defined by the virtual seeds that were "placed" during the off-line planning stage.

One disadvantage with the above approach, however, is that the trajectories defining the insertion path(s) for introducing the seeds through the skin of the patient for travel toward the target site(s) are not taken into consideration in the planning stage. Accordingly, it is very difficult to plan multiple seed deposits along a single trajectory thereby increasing the number of required needle insertions during the plan implementation phase thus increasing the associated morbidity. A lack of trajectory visualization also jeopardizes critical anatomical structures that lie between the skin and the target point.

In addition to the above, during the implementation phase, the patient must be re-scanned in the imaging apparatus, typically days later. In the likely event that the patient is not relocated onto the imaging apparatus in the position in which the patient was scanned to develop the x, y, z seed target locations during planning, the initial dose plan becomes unreliable and is therefore no longer valid. A similar disadvantageous result obtains when the tumor or other target tissue within the patient moves between the pre-operative planning scan and the implementation phase. In either case, the brachytherapist is provided with no means to adopt a new plan or otherwise adjust the original plan.

There is a need, therefore, to provide a method and apparatus for planning and executing minimally invasive procedures for in-vivo placement of objects that enables non-invasive pre-operation virtual seed placement and dose distribution planning using visualization information showing a patient's anatomy together with a set of single point targets within the patient's body and a corresponding set of trajectories through the skin and body of the patient leading to the target points.

Further, there is a need to provide a method and apparatus for planning interventional radiological procedures that provides dose distribution visualization information so that the planning interventionist can quickly and easily derive a dose plan strategy commensurate with a pathological prognosis of the patient as determined from the patient's pre-operative volumetric image data set. Preferably, the visualization information includes a cumulative dose distribution volume defining a plurality of dose level contours surrounding each virtual seed for visualization in slices taken through the patient's image volume data set at various selected angles and orientations. The dose plan preferably includes visualization information showing a prescription dose profile as well as a low dose profile surrounding the virtual seeds.

Preferably, the method and apparatus further includes a localizing device for implementing the dose plan by providing a means for precisely aligning an interventional tool along each of the one or more planning trajectories so that the radioactive seeds can be inserted at each target point and along each planning trajectory in turn according to the previously derived plan. Preferably, the method and apparatus provides visualization information in the form of at least two axial image slices showing the virtual needle entry point and target point, as well as a pair of multi-planar reformatted (MPR) image views of the patient's image data set along the trajectory of a virtual needle, each view being combined in an overlayed fashion with the dose distribution volume data set of the patient. This enables an interventionist to align the interventional tool carried on the localizing device with the virtual trajectories developed during the planning stage. The interventionist moves the localizing device and interventional tool into a range of positions relative to the patient until the multiple views of the physical tool shown on the display device are in alignment with the virtual trajectories shown on the display device and developed during the planning stage. Once aligned, the localizing device is selectively locked in place relative to the patient so that the interventional seed carrying tool can be translated along the planning trajectory to a desired depth for precise placement of the radioactive seed or other selected object within the patient's body.

SUMMARY OF THE INVENTION

In accordance with the present invention, a method and apparatus for planning a minimally invasive procedure for in-vivo placement of an object within a patient is provided.

In accordance with a more detailed aspect of the invention, a method and apparatus for planning and executing a minimally invasive procedure for in-vivo placement of an object within a patient is provided.

In accordance with yet a more detailed aspect of the invention, a method and apparatus of planning a minimally invasive procedure for in-vivo placement of a plurality of objects within the body of a patient is provided.

In accordance with yet a still more detailed aspect of the invention, a method and apparatus for planning and executing a minimally invasive procedure for in-vivo placement of a plurality of objects within the body of a patient is provided.

The preferred method of planning placement of objects within the body of a patient includes scanning the patient includes scanning the patient in an imaging device to generate a volumetric image data set of the patient. Thereafter, an image of the patient derived from the volumetric image data set is displayed on a human readable display device. A virtual target point is selected in the image of the patient by identifying a first set of virtual coordinates in the patient image. A virtual trajectory for inserting an object into the patient is selected by identifying a virtual path extending from the selected virtual target point and out from the body of the patient. Lastly, the virtual trajectory is displayed on the human readable display device together with the image of the patient. Preferably, the patient image is a multi-planar reformatted image and the image is coincident with the virtual trajectory so that the entire trajectory is visible on the display device.

The preferred apparatus for planning placement of objects within the body of a patient includes an imaging device for scanning the patient to generate a volumetric image data set of the patient. A human readable display device displays an image of the patient derived from the volumetric image data set. Processing means together with a control console are provided for selecting a virtual target point in the image of the patient and for selecting a virtual trajectory for inserting an object into the patient. The virtual target point is identified on the display device by selecting a first set of virtual coordinates in the image of the patient. The virtual trajectory is selected by identifying a virtual path extending from the selected virtual target point and extending outwardly from the body of the patient image. Lastly, a display means is provided for displaying the virtual trajectory on a human readable display device together with the image of the patient. Preferably, a multi-planar reformatted image of the patient is generated and the virtual trajectory and the planar image of the patient are coincident.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein.

DETAILED DESCRIPTION OF THE PREFERRED EMBODIMENTS

Figure 1:
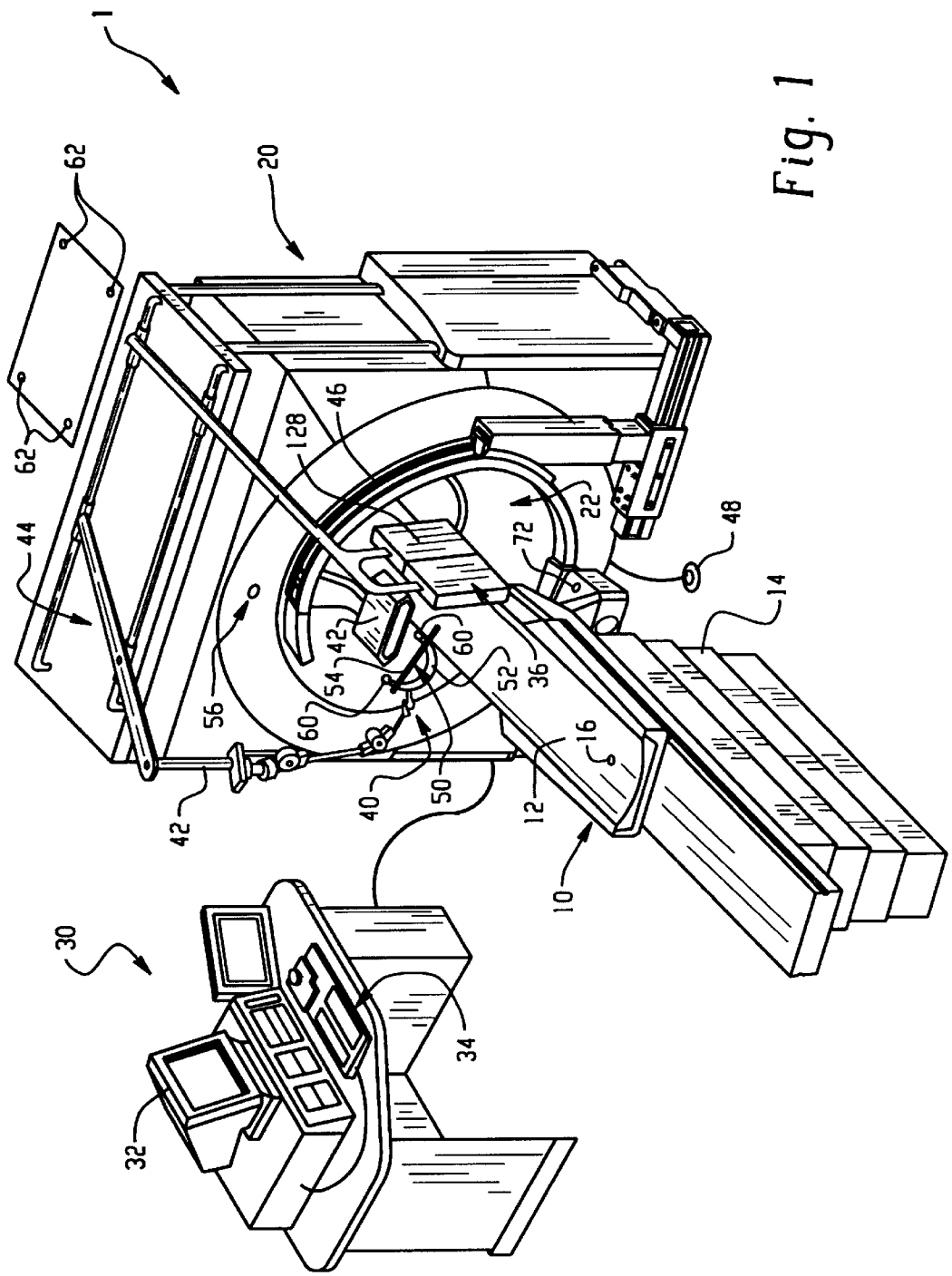
FIG. 1 is a diagrammatic illustration of a CT scanner and minimally invasive arm assembly for planning and executing procedures for in-vivo placement of objects within a patient according to the preferred embodiment of the invention.

Referring now to the drawings wherein the showings are for the purposes of illustrating the preferred embodiments of the invention only and not for purposes of limiting same, with reference first to FIG. 1, a system 1 for planning and executing minimally invasive surgical procedure for in-vivo placement of objects includes a patient table or support 10 defining a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration and verification area 16 disposed at a known, fixed location.

A planning, preferably volumetric diagnostic imaging apparatus 20 is disposed in axial alignment with the patient table such that a patient or subject on the patient support surface 12 can be moved into and through a bore 22 of the volumetric imager. In the illustrated embodiment, the volumetric imager is a CT scanner which includes an x-ray tube mounted for rotation about a preselected plane. The x-ray tube projects a fan shaped beam of radiation through a ring 24 of radiation translucent material, through the patient support 12, the a region of interest of the subject, and to a ring or arc of radiation detectors disposed opposite the x-ray tube. As the x-ray tube rotates within the plane, a series of data lines are generated, which data lines are reconstructed into at least a slice image by a reconstruction processor included in a control console 30. More specifically to the preferred embodiment, the patient support 12 moves longitudinally as the x-ray tube is rotating around the subject such that a selected volume of the patient is scanned along a spiral path or a series of slices. The position of the x-ray tube is monitored by a rotational position encoder, and the longitudinal position of the patient support is monitored by a longitudinal position encoder within the couch 10. The reconstruction processor reconstructs a volumetric image representation from the generated data lines. The control console 30 typically includes one or more monitors 32 and an operator input device 34, such as a keyboard, trackball, mouse, or the like. An interventionists control and display console 36 is supported from overhead on a track atop the CT scanner.

A mechanical arm assembly 40 is supported from overhead by a carriage 42 movable on a track system 44 affixed to the top of the volumetric diagnostic imaging apparatus 20 as generally shown. The carriage is preferably lockable in one or more predetermined fixed locations on the oval track so that a minimally invasive surgical instrument 50 carried on an interchangeable surgical instrument guidance device 52 can be positioned in monitored positions and orientations by an interventionist in preparation for and in carrying out a surgical procedure in accordance with the present invention. The surgical instrument in the illustrated embodiment includes a manually guided brachytherapy needle 54 (e.g. MICK application) adapted to engage the guidance device 52 and slide therealong to carry a radioactive seed or pellet on the tip of the needle into the body of the patient to deposit the seed at precise predetermined locations. It is to be appreciated, however, that numerous other instruments and guidance devices are contemplated.

Overall, the position and orientation of the surgical instrument 50 carried on the guidance device 52 are determined by the mechanical arm assembly 40. To that end, the mechanical arm assembly includes a plurality of arm segments which are interconnected by pivot members. Encoders or position resolvers at each joint monitor the relative articulation and rotation of the arm segments relative to each other. Position encoders or resolvers are also provided along the mechanical interconnection of the arm with the imaging apparatus 20. In this manner, the mechanical interconnection which is measured by the resolvers and encoders provides an accurate indication of the position and orientation of the guidance device 52 and the surgical instrument 50 carried thereon relative to the imaging apparatus 20.

To verify the orientation and position of the guidance device 52 relative to the patient support, a tip of the guidance device or a pointer carried thereon is touched to the calibration and verification area 16 and an assessment is made whether the electronic signals indicative of patient support location and surgical instrument location, in fact, place both at the same point in space. Similarly, one or more markers 56 on the imaging apparatus in a fixed, known location relative to the plane of rotation of the x-ray beam is touched by the tip of the guidance device or pointer and the electronic position signals are compared to be sure that the coordinate systems of the volumetric scanner 20 and the guidance device 52 are accurately correlated.

It is to be noted that mechanisms other than the arm assembly 40 and interchangeable surgical instrument guidance device 52 carried thereon are contemplated for monitoring the position of the surgical instrument 50. For example, a plurality of transmitters, such as light emitting diodes 60 are mounted on the guidance device 52 or on a localizing device (not shown) in a fixed, known relationship to the surgical instrument. An array of receivers 62 is mounted in a fixed relationship to the imaging apparatus 20, preferably affixed to the ceiling of the room. Each time the emitters are actuated and the emitted signal received by the receivers, the position and orientation of the localization device and therefore of the surgical instrument carried thereon are accurately and quickly calculated using geometric triangulation techniques. By positioning the localization device on the plurality of markers 56 disposed in a known, fixed relationship to the coordinate system of the imaging apparatus 20, the coordinate systems of the surgical instrument 50 and the imaging apparatus 20 can be readily correlated. Analogously, by positioning the localization device on the calibration and verification area 16 formed on the patient table 10, the coordinate system of the surgical instrument 50 and the patient table 10 can be readily coordinated.

Figure 2:
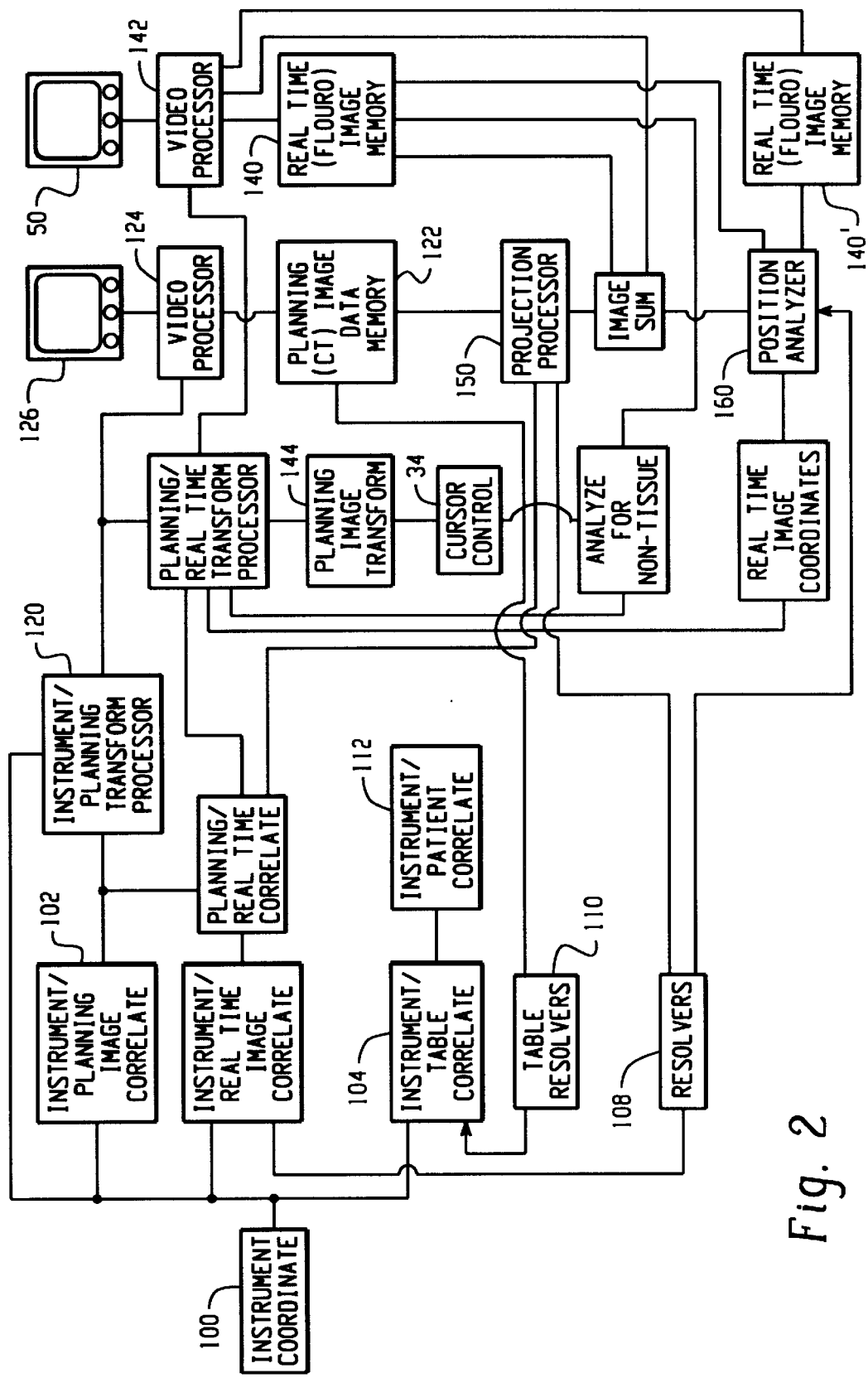
FIG. 2 is a diagrammatic illustration of the planning and implementation image processing performed in accordance with the invention using the apparatus shown in FIG. 1.

With reference to FIG. 2, an instrument coordinate circuit 100 determines the position and trajectory of the surgical instrument 50 carried on the guidance device 52 in instrument space, particularly a coordinate system of the instrument. The instrument coordinate circuit is connected with resolvers on the mechanical arm assembly 40 in the mechanical arm embodiment and with the receivers 62 in the emitter embodiment to receive signals indicative of changes of position and orientation of the instrument in instrument space. An instrument-planning scanner correlating processor 102 determines the correlation or transform between the minimally invasive surgical instrument 50 and the volumetric scanner 20 coordinate systems. The correlation or transform is normally described in terms of offset (particularly offset along the axis of the patient support), angular offset or rotation, and scaling. In one embodiment, the instrument 50 is touched to three or more markers 56 which are in a known relationship to the volumetric scanner coordinate system.

By measuring the coordinates of the instrument in the instrument coordinate system while touching each marker, three or more common points in the two coordinate systems are determined. By determining a barrycenter, centroid, or other characteristic point of the common points, the offset between the two coordinate systems is determined. By determining the angular difference between the rays from the characteristic point to each point in each coordinate system, the angular offset is determined. By determining a difference in physical displacement between the characteristic point and the corresponding points in each coordinate system, the scaling factor is determined. Of course, in a system such as the illustrated embodiment in which the instrument and the volumetric scanner are mechanically linked, the transform or relationship between the volumetric scanner and the instrument coordinate systems are determined during a calibration of the mechanical system during installation. The touching of the markers can be eliminated or used merely to confirm that the instrument and the CT scanner coordinates have not become misaligned.

An instrument-to-patient table correlating processor 104 performs a similar calculation or uses similar known physical relationships to determine the correlation or transform between the patient table and the surgical instrument. Preferably, a phantom having a multiplicity of marks is disposed in a known position on the table to provide a larger number of corresponding points in both coordinate systems for the correlating process. Images of the phantom can be used to derive transforms between the patient table space and planning or real time image coordinate systems.

Table resolvers 110 located in the patient table contribute vertical and longitudinal offsets to the correlation between the instrument and the patient table when the table is raised or lowered and when the patient support 12 is moved axially. An instrument-to-patient correlation processor 112 determines the correlation between the instrument coordinate system and a patient coordinate system. Again, this is preferably done by placing the instrument on three or more known reference points on the patient. Such points may include readily identifiable anatomical structures such as the tip of the nose, distinctive points on bones, fiducial markers that are imaged during the volumetric imaging process, or the like.

An instrument-to-volumetric image coordinate system transform processor 120 receives the correlation or transform from the instrument-to-planning scanner correlating processor 102. The instrument-to-volumetric image processor operates on input position and orientation coordinates in image space to transform them into volumetric image data space or vice-versa. Knowing the position of the surgical instrument in volumetric or planning data space enables the position of the instrument and orientation of same to be superimposed on the volumetric planning image data.

During a medical procedure, the patient is positioned in the imaging apparatus and a volumetric image data set is generated. The volumetric image data set is stored in a volumetric or planning data memory 122. The position of the patient during the generation of the planning data, particularly as the table moves to generate spiral or slice data, is stored in conjunction with the volumetric planning data such that the data is correlated with the patient table coordinate system. The operator control 30 controls the volume planning image data memory or a video processor 124 such that selected slices, projection images, surface renderings, or other conventional displays of the data are generated for display on a planning image display 126. Preferably, the planning image display includes corresponding sagittal, coronal, and transverse axial slices through one or more selected common points of intersection.

Figure 3:
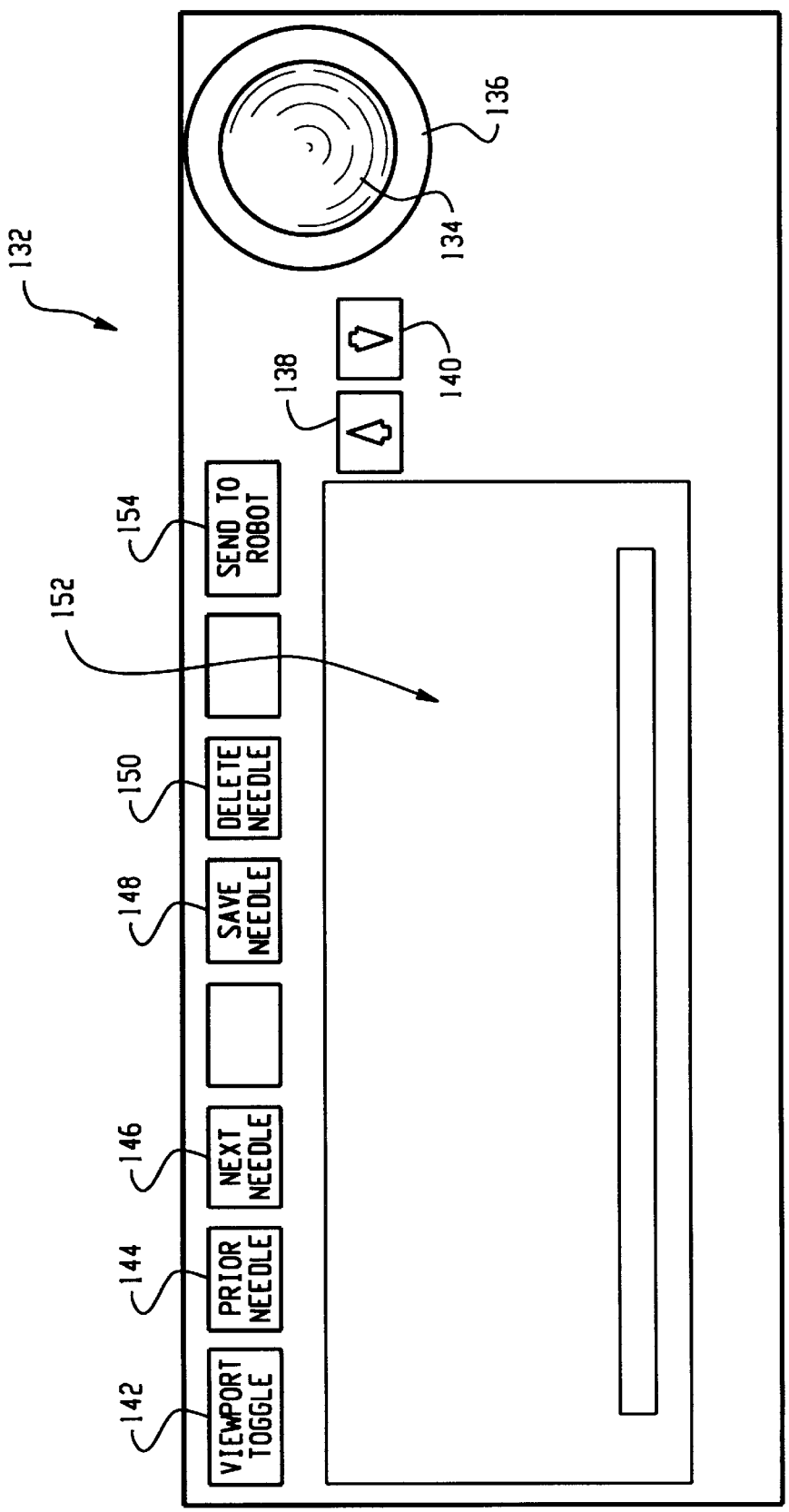
FIG. 3 is a diagrammatic illustration of a preferred set of interventionists controls for use during pre-operation planning.
Figure 4:
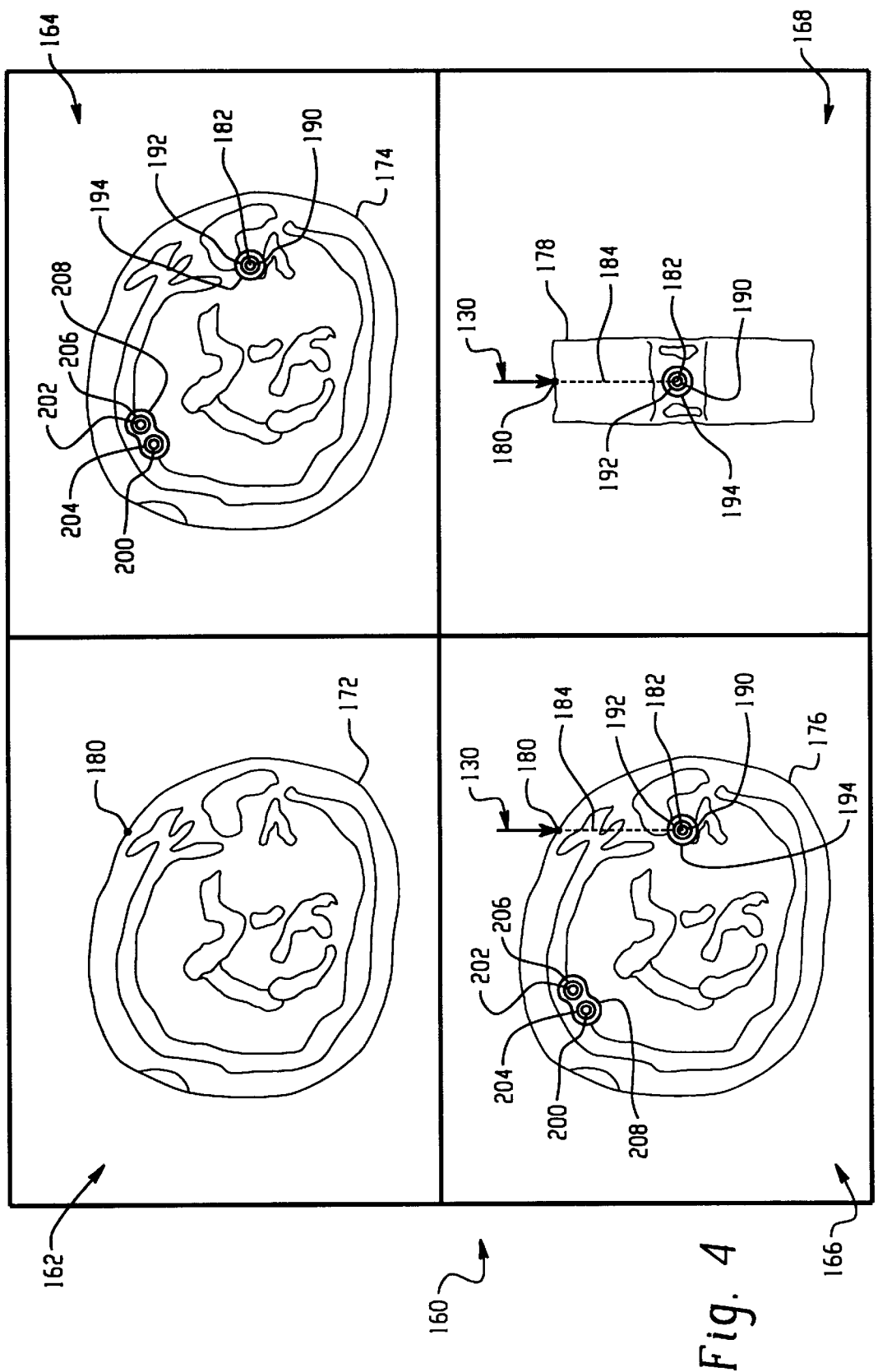
FIG. 4 is an illustration of the preferred set of images of planes extending through the patient image volume data set for use during the pre-operation planning stage of the present invention.

With reference to FIGS. 3 and 4, in accordance with the present invention, during the planning stage before implementation of an interventional surgical procedure, the movement of a virtual surgical instrument 130 is controlled and displayed as a planning image at the interventionist's control console 30. FIG. 3 is a diagrammatical illustration of a preferred set of controls 132 available to an interventionist as the operator input device at the console 30. As shown there, a track ball 134 embedded within the console is available to the interventionist to translate the virtual surgical instrument 130 relative to the planning image displayed on the planning image display 126 at the console. Rotation of the virtual surgical instrument is enabled by a theta ring 136. The length or "depth" of the virtual surgical instrument is increased using a first depth input key 138 and decreased using a second depth input key 140. A "view port toggle" input key 142 is used to select a view port as an active view port from among the set of view ports available for viewing on the display to be described below in connection with FIG. 4. A "prior needle" input key 144 and a "next needle" input key 146 are disposed on the console for selecting an active virtual surgical instrument from among a plurality of virtual surgical instruments that are displayed on the planning image display at the console for procedures involving placement of two or more radioactive seeds or other objects within the patient. The selected active virtual needle is preferably displayed in a highlighted fashion so that the interventionist can visually distinguish the active virtual needle from among the set of available but non-selected virtual needles.

A "save needle" input key 148 is provided to enable an interventionist to store a set of x, y, z coordinates in the system corresponding to the tip of the active virtual needle after it is moved to a desired location in the displayed image of the patient. The "delete needle" input key 150 deactivates the coordinates of the selected needle. Further in connection with the operator controls provided at the console 30, a keyboard portion 152 is provided to enable an operator to enter data such as comments, notes, or descriptions into the data set as desired. Lastly, a "send to robot" input key 154 is provided to enable an operator to initiate the transfer of a set of selected x, y, z coordinates of multiple target points and trajectories associated therewith to an operatively associated robotic system (not shown) for automated robotic insertion of the radioactive seeds into the patient at the appropriate locations. It is to be appreciated that the console 30 is integrated with the imaging apparatus 20.

Turning now to FIG. 4, a representative patient planning image volume display 160 is divided into four quadrants or view ports including an upper left first transverse axial view port 162, and upper right second transverse axial view port 164, a lower left proxy transverse axial to coronal view port 166, and lastly, a lower right proxy transverse axial to sagittal view port 168.

Preferably, the top two view ports 162, 164 art coordinated with the bottom two view ports 166, 168. More particularly, the top two view ports 162, 164 are axial slice images 172, 174 taken through the patient's image volume data set at the entry or insertion point 180 of the virtual needle 130 into the patient's body and at the terminus or head point 182 of the virtual needle 130 at a selected target point within the patient, respectively. Also preferably, the bottom two view ports 166, 168 are multi-planar reformatted (MPR) images 176, 178 that are co-planar with the virtual needle trajectory 184 of the virtual surgical instrument 130 to provide visualization information to the interventionist through multiple axial slices of the patient image data set along the length of the instrument trajectory.

As noted above, movement of the virtual surgical instrument is controlled at the interventionists control console 30 using the preferred set of controls 132 so that one or more selected target points can be identified within the patient's image volume data set in x, y, z coordinates. More particularly, the lower left view port 166 is an MPR image 176 of the patient showing a proxy transverse axial-to-coronal view of the patient with the virtual needle trajectory 184 extending from the virtual needle 130 between an insertion point 180 on the patient's skin and a head or target point 182. The plane defined by the proxy transverse axial-to-coronal MPR image 176 of the patient intersects the line defined by the virtual needle trajectory 184. In that way, the virtual needle trajectory 184 is co-planar with the image displayed so that the entire trajectory path can be visualized.

Similar to the above, the lower right view port 168 is an MPR image 178 of the patient showing a proxy transverse axial-to-sagittal view of the patient with the virtual needle trajectory 184 extending from the virtual needle 130 between the insertion point 180 and the head or target point 182.

The plane defined by the proxy transverse axial-to-sagittal MPR image 178 of the patient intersects the line defined by the virtual needle trajectory. In that way, the virtual needle trajectory 184 is co-planar with the image displayed so that the entire trajectory path can be visualized.

During the planning stage, if the insertion and target points 180, 182 and virtual trajectory 184 are determined to be suitable for locating a radioactive seed in the appropriate tissue while avoiding damage to the surrounding tissue along the insertion path, the interventionist presses the "save needle" input key 148 to store a set of x, y, z coordinates in the system corresponding to the tip of the virtual needle and identifying the angulation and coordinates of the physical surgical instrument 50 carried on the arm assembly 40 for exactly duplicating the path of the virtual needle trajectory with the physical instrument. If, however, either the virtual trajectory 184 or the insertion or head points 180, 182 is inappropriate or not well advised, the operator then uses the track ball 134 and/or the theta ring 136 to move the virtual needle 130 into the appropriate position and orientation to define a more appropriate insertion pathway and target point.

It is to be appreciated that as the translation and rotation keys are actuated by the interventionist, each of the images 172–178 displayed on the corresponding view ports 162–168 are simultaneously updated substantially in real time to provide the interventionist with a set of cross sectional slices through the patient's image volume data set so that suitable planning decisions can be made. One significant advantage of the invention is that major organ, veins, and other structures are visualized during the planning stage so that one or more object placement trajectories can be selected to ensure that those tissues identified are avoided during the physical object placement process.

The display 160 is used by the interventionist to select trajectories that avoid major organs, etc. The proxy transverse axial to coronal view port 166 is updated as the virtual needle is moved so that the image displayed remains co-planar with the virtual needle trajectory 184. Similarly, the proxy transverse axial to sagittal view port 168 is updated so that the displayed image is co-planar with the virtual view ports 162, 164 are updated as well. To that end, the first transverse axial view port 162 is updated to display an axial slice image of the patient that is coincident with the virtual needle. Further, each of the axial view ports 162, 164 are updated as well. To that end, the first transverse axial view port 162 is updated to display an axial slice image of the patient that is coincident with the virtual insertion point 180 and the second transverse axial view port 164 is updated to display an axial slice image that is coincident with the virtual needle head or target point 182.

With continued reference to FIG. 4, the preferred method for dose distribution planning will now be described. When the interventionist activates the "save needle" key 148, a virtual radioactive seed 190 is "deposited" in the tissue at the head point 182 of the then active virtual surgical instrument 130 and displayed as shown. substantially simultaneously therewith, the x, y, z coordinates of the virtual radioactive seeds are stored in the system and a high or "prescription" dose profile 192 is displayed surrounding the virtual radioactive seed 190 as generally shown. In addition, a low dose profile 194 is displayed surrounding the prescription dose profile 192. Preferably, in a three dimensional sense, the high and low prescription dose profiles correspond to concentrically located spheres centered on the x, y, z coordinate of the virtual radioactive seed 190. It is to be appreciated that the images shown in FIG. 4 are planar slice images taken through the patient's volumetric image data set and, accordingly, the high and low dose profiles 192, 194 appear as concentric circles. The high and low dose profiles are calculated according to known methods such as described in *A Practical Manual of Brachytherapy*, by B. Pierquin and G. Marinetto. As used herein, the expression high or prescription dose is intended to refer to a dosage intensity level intended for irradiating a tumorous mass or the like. The expression low dosage profile includes a dosage intensity intended to affect secondary tissue surrounding the cancerous or tumorous growth.

With still yet continued reference to FIG. 4, the lower left MPR image 176 illustrates the case where a pair of first and second virtual radioactive seeds 200, 202 are placed in a virtual sense during the planning phase in close proximity to each other. As illustrated, the high prescription dose profile 204 of the first radioactive seed 200 is only slightly spaced apart from the high or prescription dose profile 206 of the second radioactive seed 202 due to the small relative separation between the virtual radioactive seeds 200, 202. Where first and second virtual radioactive seeds 200, 202 are placed in close proximity to each other, the low dose profile rings surrounding the seeds overlap and are therefore represented in the planar images 174, 176 as an agglomeration 208 surrounding the pair of high dose profiles 204, 206.

Figure 5:
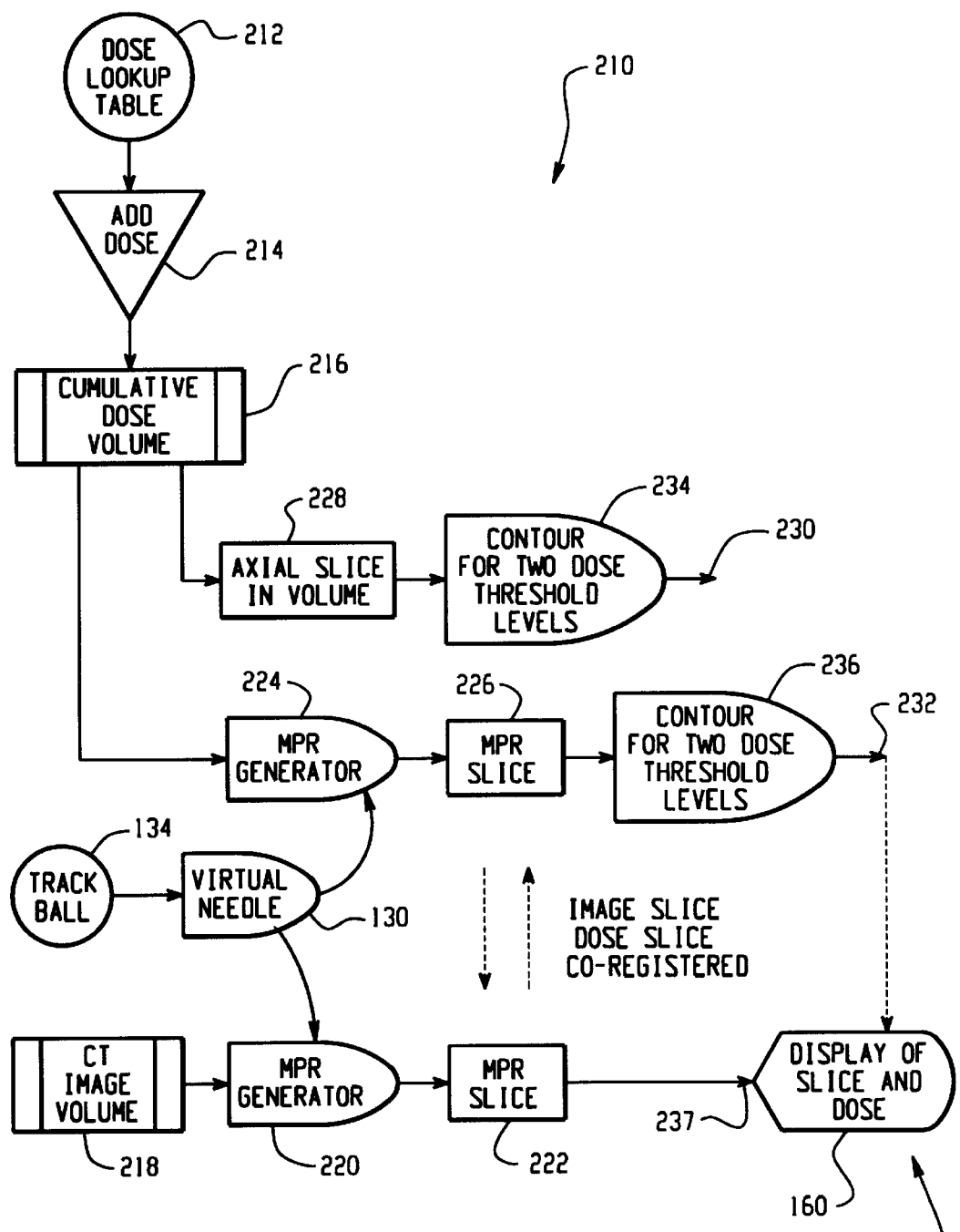
FIG. 5 is a schematic representation of a dose curve generator system in accordance with the present invention.

A schematic representation of a dose curve generator system 210 in accordance with the present invention is shown in FIG. 5. With reference now to that figure, a dose lookup table 212 is provided for storing the values of radioactive seed dose contribution at a predetermined range of distances from the source. The dose lookup table 212 is preferably derived from radioactive seed dose distribution calculations well known in the art. For each virtual radioactive seed 190 placed in the images 172–178 during the preoperative planning process, the dose lookup table 212 is accessed by an adder circuit 214 and added to a cumulative dose volume 216. Essentially, the cumulative dose volume stores the current dose level at all pixels in a volume space corresponding to the CT image volume 218 corresponding to the patient's volumetric image data set. To that end, preferably, there is a one-to-one correspondence between pixels in the cumulative dose volume 216 with pixels in the CT image volume 218.

Movement of the track ball 134 and/or theta ring 136 initiates movement of the virtual needle 130 in a manner described above to produce updated images 172–178 on the various view ports 162–168 shown on the patient planning image volume display 160. In accordance with the preferred embodiment of the invention, a first MPR generator 220 generates a first MPR slice 222 from the CT image volume 218 based on the position and orientation of the virtual needle 130. Simultaneously and substantially in parallel therewith, a second MPR generator 224 generates a second MPR slice 226 from the cumulative dose volume 216. Preferably, the first and second MPR slices 222, 226 mirror each other relative to their respective image volume sets 216, 216. Essentially, the first and second MPR slices are co-registered.

An axial slice through the cumulative dose volume 216 is calculated using an axial slice volume generator 228. With regard to the visualization of the dose distribution profile, it is to be appreciated that only a single axial slice through the cumulative dose volume 216 is needed at the transverse slice corresponding to the head point 182 of the virtual needle. It is not necessary to calculate an axial slice of the cumulative dose volume 216 at the insertion point 180 because it is unlikely that any virtual radioactive seeds 190 will be placed there (at the skin surface).

First and second dose display curves 230, 232 are generated by first and second bi-value dose contour generators 234, 236, respectively. The first and second dose display curves 230, 232 are thereafter added onto the MPR image display 237 as a combined display 238. The combined display 238 is therefore preferably the combined display of a slice taken through the CT image volume 218 together with a corresponding slice taken through the cumulative dose volume 216 with the bi-value dose contours added thereto.

Figure 6:
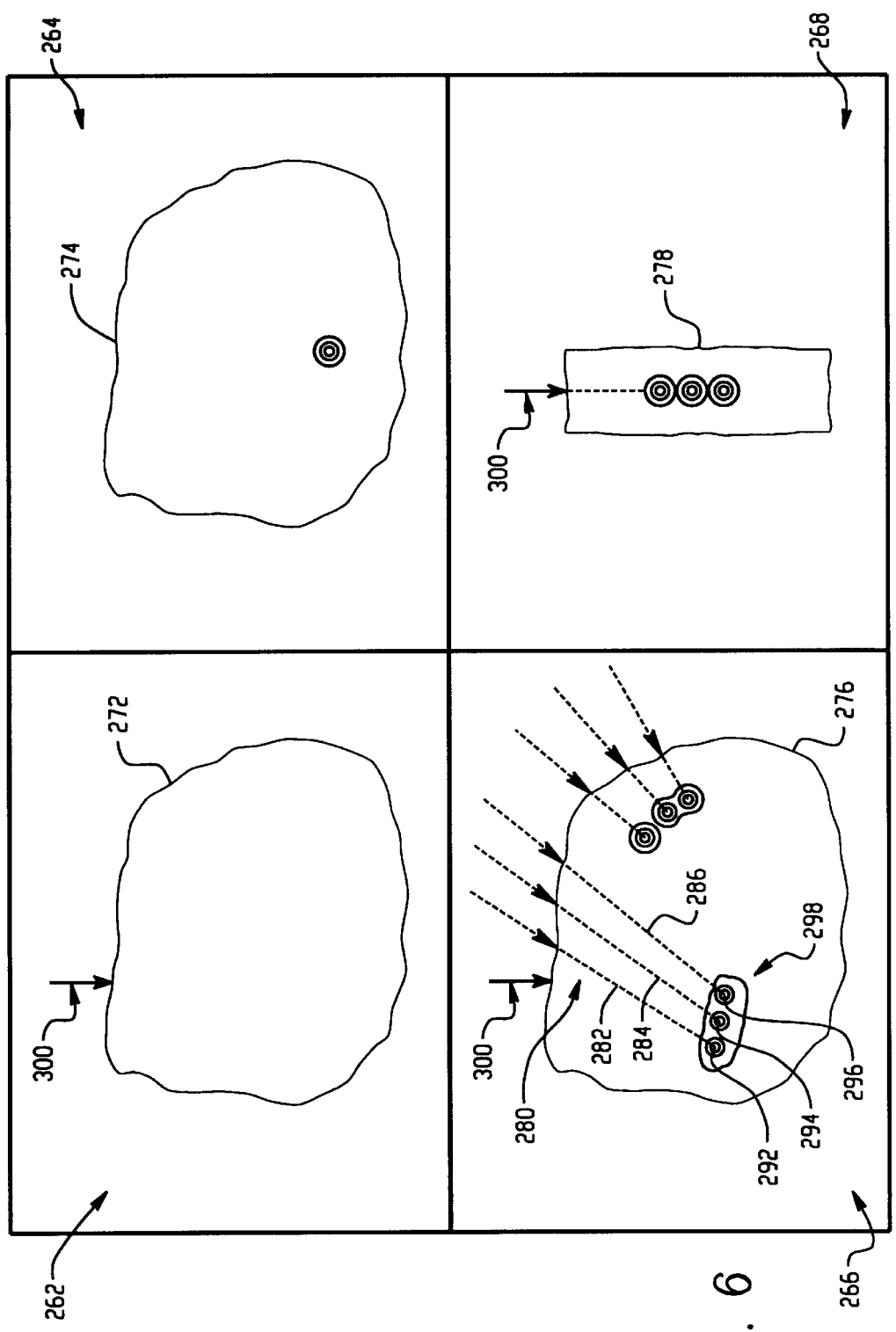
FIG. 6 is an illustration of the preferred set of images of planes extending through the patient image volume data set for use during the implementation stage of the present invention.

FIG. 6 is an illustration of the preferred set of images of planes extending through the patient image volume data set for use during the implementation stage of the present invention. Preferably, the set of images are displayed on an implementation image display 128 carried from overhead the interventionist control and display console 36 (FIG. 1) of the imaging apparatus 20. The implementation stage is the process by which physical radioactive seeds or other objects are implanted within the patient in accordance with the strategy developed during the virtual planning and visualization stage described above.

In accordance with the present invention, the implementation phase is commenced substantially immediately after the planning stage and preferably without removing the patient from the patient table 10. The figure shows a set of view ports 262–268 that display an example of a dose distribution plan in the various axial and MPR images 272–278. In that regard, the dose distribution plan shown by way of example includes a first set 280 of three virtual needle trajectories 282–286 extending through the patient image volume data set toward a corresponding set of virtual seed placement points 292–296. The seed placement points and the trajectories illustrated in the display 160 shown in FIG. 6 were determined during the planning phase in a manner as described above and are for purposes of explanation of the implementation phase of the invention. The display 260 is divided into four quadrants or view parts including an upper left first transverse axial view port 262, and upper right second transverse axial view port 264, a lower left proxy transverse axial to coronal view port 166, and lastly, a lower input proxy transverse axial to sagittal view port 268.

Also illustrated on the various images 272–278 shown on the implementation image display 128 is an image of a virtual surgical instrument 300 showing the relationship between the physical surgical instrument 50 carried on the guidance device 52 relative to the patient's anatomy supported on the patient table 10. The position and orientation of the virtual surgical instrument 300 shown on the display is continuously updated in accordance with the present invention as described in connection with FIG. 2 as the interventionist moves the guidance device 52 carried on the arm assembly 40 into various positions relative to the patient's body. The displayed virtual surgical instrument 300 essentially "tracks" the movement of the physical minimally invasive surgical instrument 50 carried on the guidance device 52. The virtual surgical instrument is preferably displayed in a highlighted portion so that the inventionist can visually distinguish the virtual instrument from the background images, including the previously identified trajectories. At implant time, the surgical instrument which is spatially referenced to the patient's image data set, acts as a needle guide to locate the one or more preplanned image planes containing the virtual object on target points. Once needle trajections are located, a physical needle, preferably a Mick needle, is advanced to the distal target coordinate along the virtual trajectory path. A digital fluoro unit shown in FIG. 1 attached to the scanner 1 is used to visualize seed drops at preplanned spacing along the needle track. The needle is withdrawn and the next preplanned trajectory is accessed with the instrument guide.

It is therefore the task of the interventionist during the early portion of the implementation phase to move the mechanical arm assembly and guidance device to position the physical surgical instrument 50 adjacent the patient's body at a position and orientation to cause the virtual surgical instrument 300 on the display to align with one of the first set of virtual needle trajectories 280 shown on the display. Preferably, the mechanical arm assembly 40 is movable into a wide range of positions and, in addition, is selectively lockable into desired fixed orientations. In that way, the guidance device 52 carried on the arm assembly 40 is able to resist offsetting forces as the interventionist advances the physical surgical instrument 50 though or along the guidance device to insert one or more objects such as radioactive seeds into a patient's body.

In the pre-planning images shown in FIG. 6, the interventionist first positions the virtual needle display 300 in alignment with the first planning trajectory 282 by manipulating the guidance device 52 carried on the mechanical arm assembly 40. Preferably, as shown in FIG. 6, the virtual needle is displayed in a format that is easily visually distinguishable from the set of planning trajectories 280 preferably through use of different colors or the like. In that way, the interventionist can easily determine when the virtual needle 300 is in alignment with the first planning trajectory 282. For true 3-dimensional representation of the virtual needle track, the image data set is reoriented into MPRs (Multi-Planar Reformatted Images). These images are derived from the patient's image data set and are angled and displayed to always contain the plane of the virtual needle in the pseudo-axial image on the lower left display 266 and is 90 degree slice counterpart (pseudo-sagittal) on the lower right display 268.

When the virtual needle 300 is in alignment with the first planning trajectory 282, the physical trajectory defined by the guidance device 52 enables insertion of a radiation therapy device, preferably a brachytherapy needle, into the patient along the pre-planning trajectory determined from the multiple view graphs of the patient's image volume data set. After placement of the first brachytherapy seed at a physical site within the patient's body corresponding to the virtual site 292, the interventionist next aligns the virtual needle 300 with the second planning trajectory 284 for insertion of a physical brachytherapy seed at a site within the patient's body corresponding to the virtual target point 294 shown on the display 266. Thereafter, a third brachytherapy seed can be inserted into the patient by first positioning the guidance device 52 into the appropriate position and orientation as guided by the view on the virtual display 266 so that a radioactive seed can be positioned within the patient's body at a physical location corresponding to the virtual target point 296.

Figure 7:
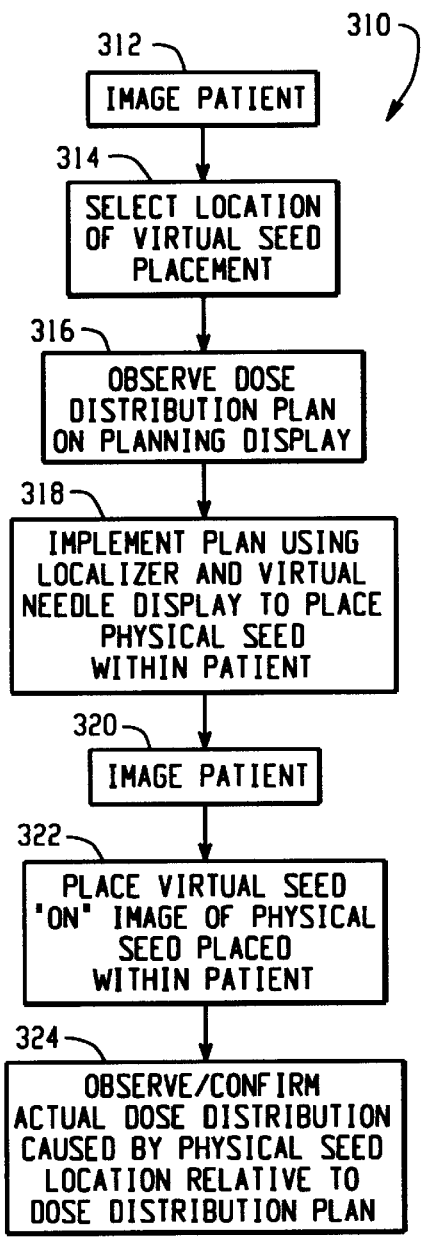
FIG. 7 is a flowchart illustrating the preferred method for planning and implementing placement of a single object within a patient's body.

Turning now to FIG. 7, the preferred method 310 for planning and implementing placement of a single radioactive seed within a patient's body will be described. Initially, as described above, the patient is imaged as a first step 312. A volumetric image data set of the patient is obtained using an imaging apparatus 20 and the resulting image is displayed on the control console 30 in a form substantially described above and shown in FIG. 4. During the planning stage, at step 314, the location of a single virtual seed 190 is selected by the planning interventionist with reference to one or more of the slice images 162–168 shown on the display 160. At step 316, the high or prescription dose profile 192 displayed on the screen is observed together with the low dose profile 194. At this point during the planning stage, the interventionist has the opportunity to modify the plan if the observed dose distribution does not correspond with the desired plan. As noted above, the "delete needle" key 150 is used to erase the selected virtual seed placement. The "save needle" key 148 is used to select a virtual seed target point 190, 200, 202 within the patient's volumetric image volume data simultaneously calculating and displaying a dose distribution curve 192, 194, 204–206 due to the one or more virtual seeds placed in the data set. Actuation of the "save needle" key 148 therefore results in the display of a virtual planning arrow 130, a virtual planning trajectory 184, a virtual seed placement location 190, a high dose distribution display 192, and, lastly, a low dose distribution display 194.

If the virtual seed placement together with the high and low dose profiles are satisfactory to the interventionist, the seed placement implementation phase is initiated at step 318. For this, the interventionist uses the image of a virtual surgical instrument 300 shown on the implementation image display 128 in a manner described above to position the physical surgical instrument 50 relative to the patient's body so as to cause an alignment between the virtual surgical instrument 300 shown on the display with the virtual planning arrow 130. As noted above, the mechanical arm assembly 40 is selectively lockable into various positions so as to enable the interventionist to easily move the arm to enable alignment between the virtual plan needle 130 with the image 300 of the physical needle and lock the arm for use in guiding the brachytherapy needle along the desired trajectory into the patient's body.

After the physical radioactive seed is placed within the patient's body, the patient is once again imaged as step 320 using the imaging device 20 or an associated digital fluoro unit attached to the device. Of course, the physical radioactive seed will be evident in the resultant image 160 displayed at the operator's console 30. In order to confirm the correct placement of the physical seed at the desired location within the patient, the interventionist merely places a virtual seed "on" the image of the physical seed in step 322. More particularly, the interventionist uses the set of controls 132 provided at the console 30 to move a virtual needle 130 so that a virtual seed is deposited in the patient's image volume data set at an x, y, z coordinate location corresponding to the image of the physical seed. After the virtual needle is in place the interventionist activates the "save needle" 148 key on the controls whereupon a high or prescription dose profile 192 is illustrated together with a low dose profile 194. Of course, since the virtual seed location is coincident with the image of the physical seed, the dose distribution profiles 192, 194 accurately reflect the actual physical dose distribution profile for the seed previously placed. At step 324, the interventionist observes and confirms the actual dose distribution caused by the physical seed location relative to the original dose distribution plan.

Figure 8:
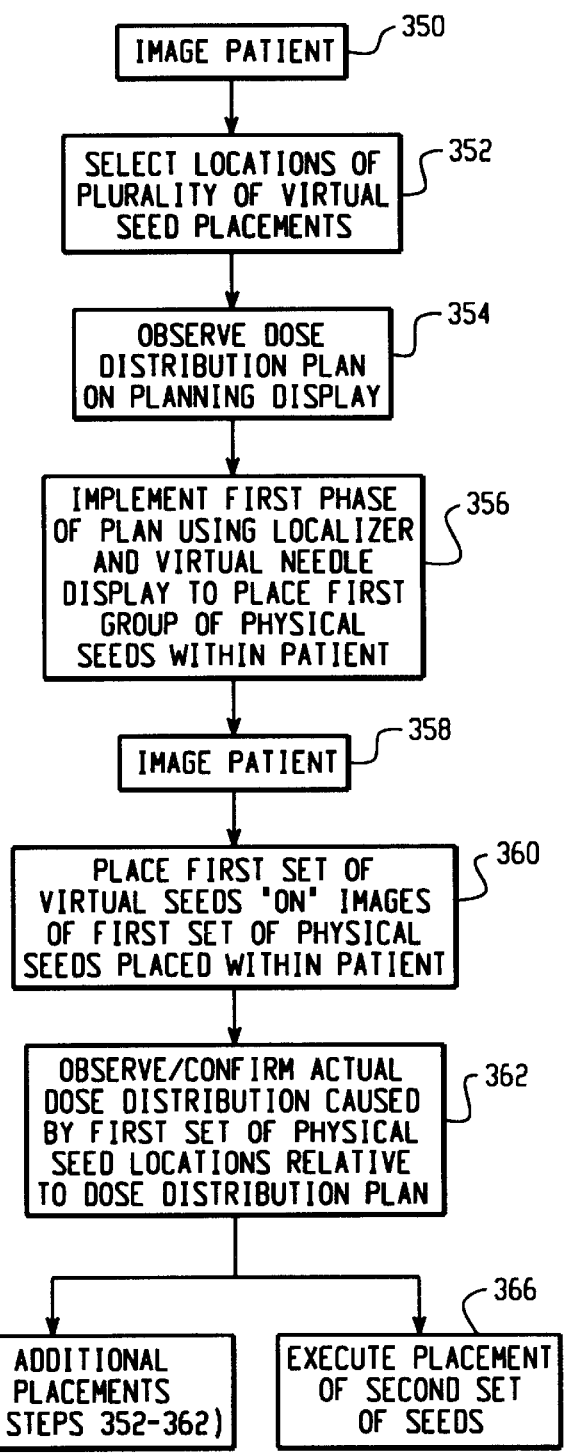
FIG. 8 is a flowchart illustrating the preferred method for planning and implementing placement of a plurality of objects within a patient's body; and, FIG. 9 is a view graph illustrating an actual dose distribution realized after executing the implementation stage for locating a first set of objects within a patient's body.

FIG. 8 is a flowchart illustrating the preferred method for planning and implementing placement of a plurality of objects within a patient's body. As will be described below, it is a significant advantage of the present invention that the planning and implementation of the placement of a plurality of objects within the body of a patient is selectively executable in a piece-wise fashion. More particularly, as will become apparent below, the preferred method of the present invention enables the interventionist to selectively toggle between planning and implementation phases so that the radioactive seeds can be piece-wise placed within the patient's body in small groups of, for example, two seeds or more so that, as the seeds are placed in groups, the actual dose distribution profiles can be observed and confirmed (or found to be misplaced) as the process proceeds. The dose distribution caused by misplaced seeds can be corrected by the strategic placement of subsequent additional seeds.

With particular reference now to FIG. 8, the patient is imaged at step 350. Next, at step 352, the locations of a plurality of virtual seed placements are selected using the controls 132 at the console 30 in a manner described above. The plurality of locations of virtual seed placements are observable to the interventionist such as shown in the view graph 266 shown in FIG. 6. Together with the location of the seed placements 292–296, the dose distribution plan 298 is observed at step 354.

Next, when the interventionist has confirmed that the correct placement of the virtual seeds within the patient image, together with the appropriate dose distribution plan, the seed placement implementation phase is commenced at step 356. More particularly, in accordance with the invention, a first phase of the dose distribution plan is implemented at step 356 using the localizer and virtual needle display to place a first group of physical seeds within the patient. As an example, the interventionist places a first group of physical seeds corresponding to the virtual seeds 292–296.

After placement of the seeds within the patient in a manner described above, the patient is once again imaged in the imaging device 20 or by using a digital fluoro unit operatively connected with the device. Next, at step 360, the interventionist places a first set of virtual seeds "on" images of the first set of physical seeds placed within the patient. In a manner described above, high and low dose profiles 192, 194 are automatically generated in the view graphs displayed at the interventionist's console 30. At step 362, the interventionist observes and confirms the actual dose distribution caused by the first set of physical seeds within the patient relative to the original dose distribution plan.

It is an advantage of the present invention that when the actual dose distribution realized by the physical placement of the first group of radioactive seeds matches the original dose distribution plan, the interventionist can proceed to the implementation phase at step 366 for placing a second, third, etc. group of radioactive seeds following the method shown in FIG. 8. On the other hand, when the actual dose distribution does not match the plan dose distribution, the interventionist selectively re-enters the planning phase at step 364 for selecting the location of an additional virtual seed placement so that the original dose distribution plan can be faithfully executed.

Figure 9:
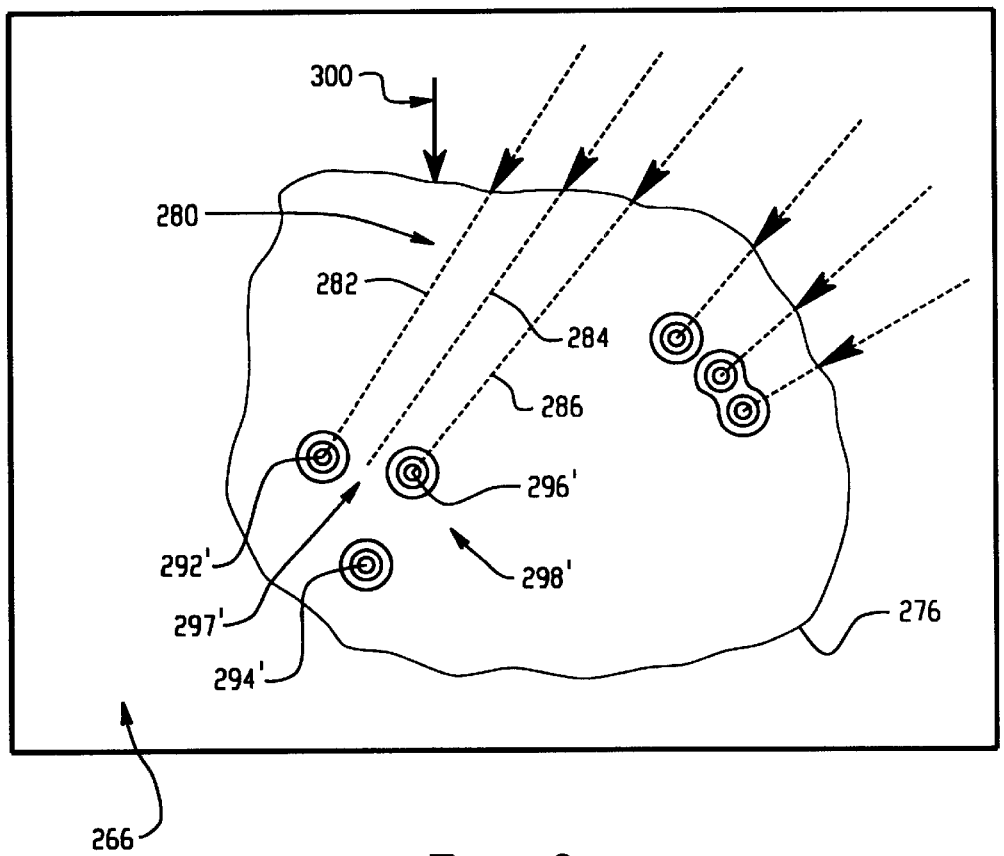

As an example of the above, FIG. 9 illustrates an example of an MPR image showing a group of seeds that were malpositioned within the patient's body. As shown there, the second seed 294' was inadvertently mislocated within the patient relative to the original plan location 294 shown in the view graph 266 FIG. 6. As can be seen, the resultant dose distribution 298' is significantly different from the original dose distribution plan 298 shown in the view graph 266 of FIG. 6. Essentially, a "cold spot" 297 is formed between the first and third seed placement locations 292', 296'. In this example, in accordance with the present invention, the interventionist is provided with the opportunity at step 364 to plan the placement of an additional virtual seed at a location substantially corresponding to the original x, y, z coordinate location of the second seed 294. Placement of an additional seed there remedies the "cold spot" and enables an actual implementation of the original dose distribution plan shown in FIG. 6.

The invention has been described with reference to the preferred embodiments. Obviously, modifications and alterations will occur to others upon reading and understanding the preceding detailed description. It is intended that the invention will be construed as including all such modifications and alterations insofar as they come within the scope of the appended claims or the equivalents thereof.

Having thus described the invention, it is claimed:

1. An apparatus (1) for planning placement of objects within the body of the patient by a minimally invasive procedure, the apparatus comprising:

an image device (20) scanning the patient to generate a volumetric image data set of the patient;

a human readable device (32, 36, 128) for displaying an image (162) of the patient derived from said volumetric image data set;

means (132–154) for selecting a virtual target point (182) in said image of the patient by identifying a first set of virtual coordinates in said image of the patient;

means (132–154) for selecting a virtual trajectory (184) for inserting an object into said patient by identifying a virtual path extending from said selected virtual target point (182) and out from the body of the patient; and, display means (164, 166, 168) for displaying said virtual trajectory (184) from said selected virtual target point and out from the body of the patient on said human readable display (32, 36, 128) together with said image (162) of the patient.

2. The apparatus according to claim 1 wherein the display means for displaying the virtual trajectory (184) includes:

means for developing a multi-planar reformatted image (166, 168) of the patient; and, means for displaying a planar image of the patient coincident with said virtual trajectory (184).

3. The apparatus according to claim 1 further including means (210) for displaying a virtual prescription dose profile (192) surrounding the selected virtual target point (182) in said image of the patient.

4. The apparatus according to claim 1 further including a memory for storing, said first set of virtual coordinates corresponding to said selected virtual target point in said image of the patient and, information corresponding to said selected virtual trajectory.

5. The apparatus according to claim 4 further including:

means for selecting a plurality of virtual target points in said image of the patient by identifying a plurality of sets of virtual coordinates in said image of the patient; and, means for selecting a plurality of virtual trajectories for inserting objects into said patient by identifying a corresponding plurality of virtual paths extending from said plurality of virtual target points and out from the body of the patient.

6. The apparatus according to claim 5 further including means for displaying a plurality of virtual prescription dose profiles surrounding said plurality of selected virtual target points in said image of the patient.

7. A method of planning placement of objects within the body of the patient by a minimally invasive procedure, the method comprising the steps of:

scanning the patient in an imaging device (20) to generate a volumetric image data set of the patient;

displaying on a human readable device (32, 36, 128) an image (162, 164, 166, 168) of the patient derived from said volumetric image data set;

selecting a virtual target point (182) in said image of the patient by identifying a first set of virtual coordinates in said image of the patient;

selecting a virtual trajectory (184) for inserting an object into said patient by identifying a virtual path extending from said selected virtual target point (182) and out from the body of the patient; and, displaying said virtual trajectory (184) from said selected virtual target point and out from the body of the patient on said human readable display (32, 36, 128) together with said image of the patient.

8. The method according to claim 7 wherein the step displaying the virtual trajectory (184) includes:

developing a multi-planar reformatted image of the patient; and, displaying a planar image of the patient coincident with said virtual trajectory (184).

9. The method according to claim 7 further including the step of displaying a virtual prescription dose profile (192) surrounding the selected virtual target point (182) in said image of the patient.

10. The method according to claim 7 further including the steps of:

storing, in a memory of said imaging device, said first set of virtual coordinates corresponding to said selected virtual target point in said image of the patient; and, storing, in said memory, information corresponding to said selected virtual trajectory.

11. The method according to claim 10 further including the steps of:

selecting a plurality of virtual target points in said image of the patient by identifying a plurality of sets of virtual coordinates in said image of the patient; and, selecting a plurality of virtual trajectories for inserting objects into said patient by identifying a corresponding plurality of virtual paths extending from said plurality of virtual target points and out from the body of the patient.

12. The method according to claim 11 further including the step of displaying a plurality of virtual prescription dose profiles surrounding said plurality of selected virtual target points in said image of the patient.

13. A method for use with an imaging apparatus for minimally invasive placement of objects within a patient, the method comprising the steps of:

providing visualization information of the patient on a human readable display associated with said imaging apparatus, the visualization information showing at least one interventional therapy object placement target point within said patient, and at least one planning therapy trajectory extending through the patient from the object placement target point;

providing an interventional therapy tool carried on a localizing device of the imaging apparatus;

displaying the interventional therapy tool on said human readable display as a virtual tool image together with said visualization information of said patient;

manually moving the localizing device relative to the patient to align the virtual tool image with said planning therapy trajectory; and, after the virtual tool image is aligned with said planning therapy trajectory, locking the localizing device in place so that an interventional therapy object can be translated along said planning therapy trajectory to a desired depth for precise placement of said interventional therapy object at said object placement target point within said patient.

14. The method according to claim 1 wherein the step of providing said visualization information includes:

providing at least one axial planar image slice of the patient showing said object placement target point within the patient; and, providing at least one multi-planar reformatted image view of the patient oblique to said axial planar image slice, the at least one multi-planar reformatted image view containing said at least one planning therapy trajectory.

15. The method according to claim 14 wherein the step of displaying said interventional therapy tool on said human readable display as a virtual tool image includes overlaying the virtual tool image on said visualization information of the patient on said human readable display.

16. The method according to claim 15 wherein:

the step of displaying said virtual tool image includes displaying said virtual tool image on said human readable display in a manner to visually distinguish the virtual tool image from said visualization information of the patient.

17. The method according to claim 13 further including the steps of:

providing a minimally invasive surgical tool adapted for movement relative to the localizing device and carrying at least one of said objects;

advancing the tool along said planning therapy trajectory; and, depositing said at least one object within said patient at said target point.

18. The method according to claim 17 further including the steps of:

imaging the patient using said imaging apparatus to generate second visualization information of the patient and said at least one object;

displaying the second visualization information on said human readable display; and, identifying a dose distribution on said human readable display.

19. The method according to claim 13 further including the steps of:

generating a dose distribution profile surrounding the target point; and, displaying said dose distribution profile on said human readable display.

* * * * *